United States Patent
L'Huillier et al.

(10) Patent No.: US 11,266,696 B2
(45) Date of Patent: Mar. 8, 2022

(54) METHOD OF TREATING STEM CELLS WITH NAD

(71) Applicant: AMERICORD REGISTRY LLC, New York, NY (US)

(72) Inventors: Andrew L'Huillier, Edison, NJ (US); Ayanna Bryan, Bloomfield, NJ (US); Martin Smithmyer, New York, NJ (US)

(73) Assignee: AMERICORD REGISTRY LLC, New York, NY (US)

( * ) Notice: Subject to any disclaimer, the term of this patent is extended or adjusted under 35 U.S.C. 154(b) by 220 days.

(21) Appl. No.: 16/748,390

(22) Filed: Jan. 21, 2020

(65) Prior Publication Data

US 2020/0230175 A1 Jul. 23, 2020

Related U.S. Application Data

(60) Provisional application No. 62/794,077, filed on Jan. 18, 2019.

(51) Int. Cl.
*A61K 35/28* (2015.01)
*A01N 1/02* (2006.01)
*A61K 9/00* (2006.01)

(52) U.S. Cl.
CPC ............ *A61K 35/28* (2013.01); *A01N 1/0226* (2013.01); *A61K 9/0019* (2013.01); *A61K 9/0085* (2013.01)

(58) Field of Classification Search
None
See application file for complete search history.

(56) References Cited

U.S. PATENT DOCUMENTS

2018/0051253 A1* 2/2018 Chen ................... C12N 5/0647
2018/0362570 A1* 12/2018 Ganapati ................ A61P 29/00

FOREIGN PATENT DOCUMENTS

WO   WO 2018/088821   *  5/2018

OTHER PUBLICATIONS

Panuganti, S. et al. Nicotinamide Increases the Megakaryocytic Maturation of Human Hematopoeitic Stem Cells . . . Blood 112(11) 850-851, Nov. 16, 2008. (Year: 2008).*
Domen J. et al. Self-Renewal, Differentiation or Death. Molecular Medicine Today 5:201-208, May 1999. (Year: 1999).*

* cited by examiner

*Primary Examiner* — Ralph J Gitomer
(74) *Attorney, Agent, or Firm* — Bond Schoeneck & King, PLLC; George McGuire

(57) ABSTRACT

Methods for the ex vivo use of NAD to remove T cells that can potentially cause graft-verus-host disease (GvHD) from hematopoietic stem cell sources. Hematopoietic stem cell sources include bone marrow, cord blood, and peripheral blood (including mobilized peripheral blood). The present invention is a method including steps for using the hematopoietic stem cell sources treated with NAD for hematopoietic stem cell transplants (HSCTs). HSCTs are used as the standard-of-care in many diseases including several types of cancer and several genetic disorders. The majority of these transplants are allogeneic, in which the stem cell source comes from a donor who is a different individual than the intended recipient. Allogeneic HSCTs carry a risk of causing GvHD, in which donor T cells attack the recipient.

18 Claims, 1 Drawing Sheet

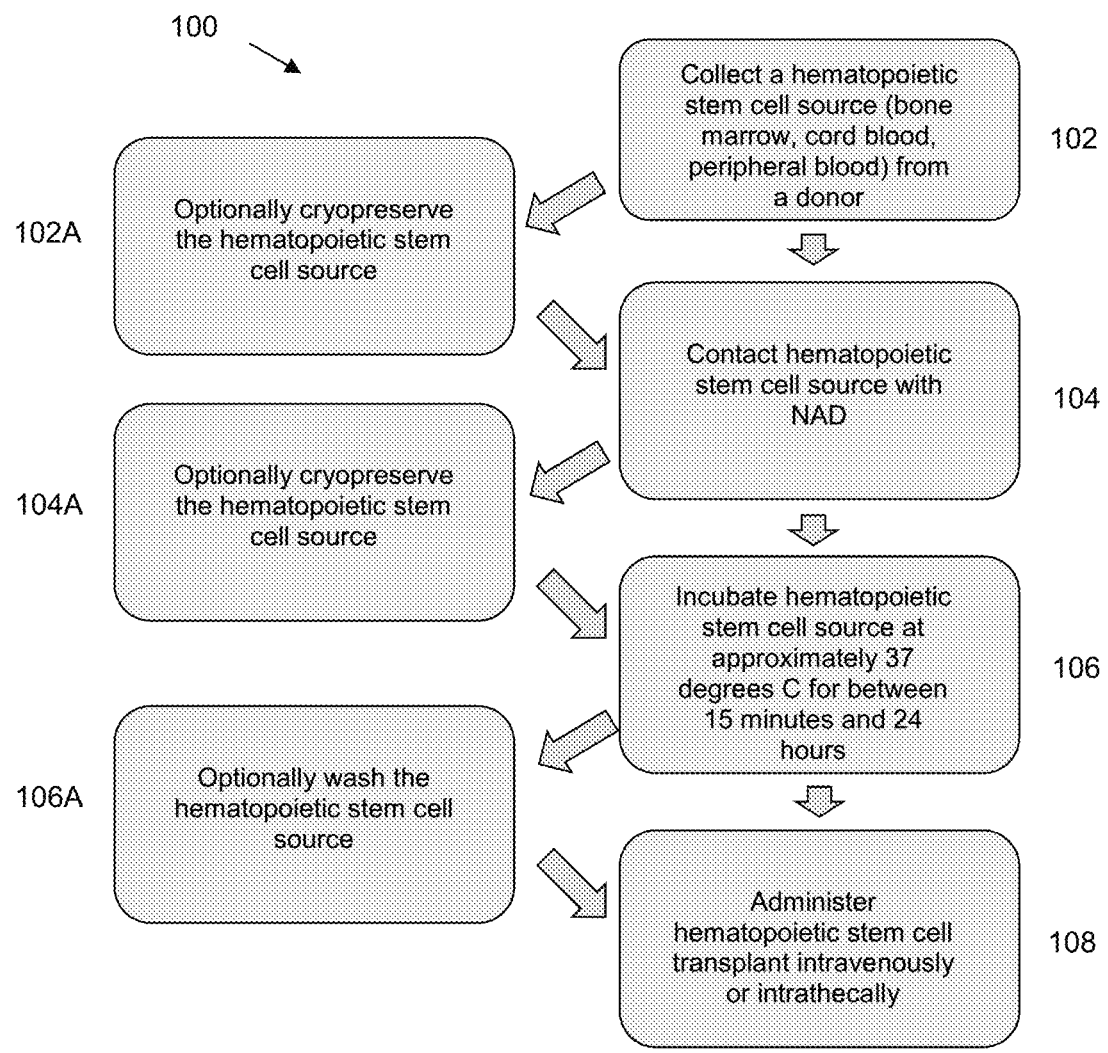

METHOD OF TREATING STEM CELLS WITH NAD

CROSS-REFERENCE TO RELATED APPLICATION

The present application claims priority to and the benefit of U.S. Provisional Patent Application No. 62/794,077, filed on Jan. 18, 2019 and entitled "Method of Preparing a Stem Cell Source with Reduced Graft Versus Host Disease Risk and Methods of Using the Same," the entirety of which is incorporated herein by reference.

BACKGROUND OF THE INVENTION

1. Field of the Invention

The present disclosure is directed generally to hematopoietic stem cell transplants and, more particularly, to ex vivo use of NAD to remove T cells.

2. Description of Related Art

Hematopoietic stem cell transplants (HSCT) involve taking a hematopoietic stem cell source from a donor and using it to treat a recipient. In the majority of cases, the donor is a different individual than the recipient, in which case the transplant is termed "allogeneic." Allogeneic HSCTs carry a risk of graft-versus-host disease (GvHD) in which donor T cells attack the recipient. GvHD can be acute, where the symptoms are sudden, or chronic, where the symptoms are ongoing. Acute GvHD can generally be managed using anti-inflammatory drugs, and the disease will eventually subside. Chronic GvHD, on the other hand, often does not subside, or only subsides after extended periods, and requires long-term management. Both acute and chronic GvHD are potentially life threatening and greatly impair patient quality of life. Chronic GvHD is additionally very expensive as it requires long-term managed care and predisposes patients to infections. Human leukocyte antigens (HLA) matching the donor and recipient of the HSCT can improve GvHD outcomes by reducing risk and severity, but the requirement for HLA matching results in long wait times for patients to find an HLA match close enough to be treated. This wait can often be long enough that the patient dies of his or her condition before they can be treated.

A method to prevent GvHD caused by HSCT would be of great benefit both to patients who would receive lifesaving treatments faster and with fewer side effects, and to healthcare systems which must pay not only for the transplant itself, but also for the management of patient morbidity and mortality related to GvHD. Several methods have been investigated to reduce the chance or severity of GvHD. One broad category of these methods includes depletion of T cells. GvHD is caused by donor T cells which reside in the stem cell source along with hematopoietic stem cells rather than the stem cells the transplant aims to take advantage of, and the selective removal of T cells reduces GvHD risk.

Several problems exist in the art with a strategy that aims to remove T cells from the stem cell source. The first problem involves the methods for T cell removal. Removal is achieved using methods known as sorting, where devices such as a flow cytometer or magnetic beads are used to separate T cells from the remaining cells in the stem cell source. These devices are often damaging to all cells in the stem cell source, including the stem cells, and increase the risk of contamination with pathogens. A second issue with removing all donor T cells is the increased risk of infection. Recipients of HSCTs have often received drugs that deplete their own hematopoietic stem cells, making them unable to make new white blood cells, and putting them at risk of infection. T cells within the HSCT can partially protect these patients while the hematopoietic stem cells from the donor repopulate the bone marrow of the recipient. Thus, removal of these T cells prevents this protection. Ideally, a method of preventing GvHD in HSCTs would involve removal of T cells that cause GvHD, but not removal of T cells that help protect against pathogens.

Therefore, there is a need for an improved method for reducing or eliminating the risk of GvHD.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a method of treating a hematopoietic stem cell source. According to one aspect, the method includes the steps of: (i) collecting a hematopoietic stem cell source comprising T cells; (ii) contacting said hematopoietic stem cell source with a concentration of NAD; and (iii) incubating the hematopoietic stem cell source to induce apoptosis of at least some of the T cells.

According to another aspect, the method includes the step of cryopreserving the hematopoietic stem cell source after collection.

According to yet another aspect, the method includes the step of cryopreserving the hematopoietic stem cell source after contact with NAD.

According to an additional aspect, the method includes the step of washing the hematopoietic stem cell source after the hematopoietic stem cell source is incubated.

These and other aspects of the invention will be apparent from and elucidated with reference to the embodiment(s) described hereinafter.

BRIEF DESCRIPTION OF THE DRAWING

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which:

FIG. 1 is a flowchart of a method of treating a hematopoietic stem cell source.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

NAD (nicotinamide adenine dinucleotide) is a cofactor of many chemical reactions inside cells and is critical for metabolism. However, when released outside of cells, NAD acts as a damage-associated molecular pattern (DAMP). DAMPs (alternatively termed "alarmins") trigger and perpetuate a non-infectious inflammatory response. Treatment of cells with NAD leads to ART2.2 mediated ADP-ribosylation of cell surface proteins including the purinergic receptor P2X7, leading to its activation. On T cells, P2X7 activation by NAD and ART2.2 causes apoptosis (i.e., cell death). However, upon T cell activation, ART2.2 is shed from the cell surface, making these activated T cells resistant to NAD-mediated apoptosis. In an HSCT, donor T cells that ultimately cause GvHD are typically naive T cells. Memory T cells have a greater chance of specificity to pathogens. This is likely because donor T cells have generally not been previously exposed to cells of the recipient, while the donor will have been exposed previously to various pathogens.

Referring now to the FIGURES, wherein like reference numerals refer to like parts throughout, FIG. 1 shows a flowchart of a method 100 of treating a hematopoietic stem cell source. The present invention includes a method 100 of treating a hematopoietic stem cell source, including bone marrow, cord blood, or peripheral blood, to reduce or eliminate the risk or severity of GvHD. The method 100 includes the first step 102 of collecting a hematopoietic stem cell source (e.g., bone marrow, cord blood, peripheral blood) from a donor. In an embodiment wherein the hematopoietic stem cell source is peripheral blood, the peripheral blood is optionally taken from a patient who was treated with one or more proteins or chemicals to mobilize hematopoietic stem cells from the bone marrow into the peripheral blood, also known as mobilized peripheral blood. Methods to mobilize hematopoietic stem cells to peripheral blood include injection of the donor with the protein G-CSF and the chemical plerixafor (trade name Mozobil®). At step 102A, an optional step, the hematopoietic stem cell source is the subject to cryopreservation.

The hematopoietic stem cell source (or cryopreserved hematopoietic stem cell source) is then contacted with NAD at the next step, step 104. The hematopoietic stem cell source (e.g., cord blood) is contacted with a concentration of NAD sufficient to induce apoptosis in at least some of the T cells contained within the stem cell source, and with minimal induction of apoptosis in the hematopoietic stem cells contained in the stem cell source. In an embodiment, the concentration of NAD is at least 1 µM. In a preferred embodiment, the concentration of NAD is at least 1 mM. In an alternative embodiment, the concentration of NAD is as much as 1 M. The hematopoietic stem cell source may be subject to cryopreservation, at step 104A, after the hematopoietic stem cell source has been contacted with NAD or prior to the administration of NAD (at step 102A shown in FIG. 1).

At step 106, the NAD-contacted hematopoietic stem cell source is incubated at normothermic temperatures of approximately 37° C. The incubation period is for a length of time sufficient for the NAD to activate P2X7 receptors on the T cells and induce apoptosis. This time is a period of 15 minutes up to and including 24 hours. At optional step 106A, the hematopoietic stem cell source is washed before infusion into the patient.

Finally, at step 108, the hematopoietic stem cell source is infused into the patient. In on embodiment, the hematopoietic stem cell source is infused intravenously into the patient. In an alternative embodiment, the hematopoietic stem cell source is infused into the patient intrathecally. The hematopoietic stem cell source can be given to a patient for any disease or condition for which an HSCT is an acceptable treatment, of which many are known. Additionally, the hematopoietic stem cell source can be given to a patient for a condition which is determined to be treatable with HSCT for which current treatments do not include HSCT as the standard-of-care. The present invention recognizes that diseases and conditions treatable with the described hematopoietic stem cell sources are rapidly being discovered and advancing.

While embodiments of the present invention have been particularly shown and described with reference to certain exemplary embodiments, it will be understood by one skilled in the art that various changes in detail may be affected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method for treating a hematopoietic stem cell source to induce apoptosis, comprising the steps of:
   collecting a hematopoietic stem cell source comprising T cells;
   contacting said hematopoietic stem cell source with a concentration of NAD; and
   incubating the hematopoietic stem cell source to induce apoptosis of at least some of the T cells.

2. The method of claim 1, wherein the hematopoietic stem cell source is at least one of bone marrow, cord blood, and peripheral blood.

3. The method of claim 2, wherein the peripheral blood is mobilized peripheral blood.

4. The method of claim 1, wherein the hematopoietic stem cell source is incubated at 37° C.

5. The method of claim 1, wherein the hematopoietic stem cell source is incubated for a time sufficient for NAD to induce apoptosis.

6. The method of claim 1, further comprising the step of cryopreserving the hematopoietic stem cell source after the hematopoietic stem cell source is contacted with NAD.

7. The method of claim 1, further comprising the step of cryopreserving the hematopoietic stem cell source before the hematopoietic stem cell source is contacted with NAD.

8. The method of claim 1, further comprising the step of washing the hematopoietic stem cell source after the hematopoietic stem cell source is incubated.

9. The method of claim 1, further the comprising of treating a patient with the hematopoietic stem cell.

10. The method of claim 9, wherein the hematopoietic stem cell source is administered to the patient intravenously.

11. The method of claim 9, wherein the hematopoietic stem cell source is administered to the patient intrathecally.

12. The method of claim 1, wherein the concentration of NAD is within a range of 1 µM to 1 M.

13. The method of claim 1, wherein incubating is within a range of 15 minutes to 24 hours.

14. The method of claim 1, wherein the hematopoietic stem cell source is allogenic.

15. A method for treating a hematopoietic stem cell source to induce apoptosis, comprising the steps of:
- collecting a hematopoietic stem cell source comprising T cells;
- cryopreserving the hematopoietic stem cell source after collection;
- contacting said hematopoietic stem cell source with a concentration of NAD; and
- incubating the hematopoietic stem cell source to induce apoptosis of at least some of the T cells.

16. The method of claim 15, further comprising the step of washing the hematopoietic stem cell source after the hematopoietic stem cell source is incubated.

17. A method for treating a hematopoietic stem cell source to induce apoptosis, comprising the steps of:
- collecting a hematopoietic stem cell source comprising T cells;
- contacting said hematopoietic stem cell source with a concentration of NAD;
- cryopreserving the hematopoietic stem cell source after contact with NAD; and
- incubating the hematopoietic stem cell source to induce apoptosis of at least some of the T cells.

18. The method of claim 17, further comprising the step of washing the hematopoietic stem cell source after the hematopoietic stem cell source is incubated.

* * * * *